United States Patent
Breininger et al.

(10) Patent No.: US 11,883,108 B2
(45) Date of Patent: Jan. 30, 2024

(54) METHOD FOR DEFORMATION SIMULATION AND APPARATUS

(71) Applicant: Siemens Healthcare GmbH, Erlangen (DE)

(72) Inventors: Katharina Breininger, Erlangen (DE); Marcus Pfister, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 686 days.

(21) Appl. No.: 16/943,037

(22) Filed: Jul. 30, 2020

(65) Prior Publication Data
US 2021/0030475 A1 Feb. 4, 2021

(30) Foreign Application Priority Data
Jul. 31, 2019 (EP) ..................................... 19189356

(51) Int. Cl.
 *A61B 34/10* (2016.01)
 *G06T 7/11* (2017.01)
 (Continued)

(52) U.S. Cl.
 CPC .............. *A61B 34/10* (2016.02); *G06F 30/27* (2020.01); *G06T 7/11* (2017.01); *G16H 30/40* (2018.01);
 (Continued)

(58) Field of Classification Search
None
See application file for complete search history.

(56) References Cited

U.S. PATENT DOCUMENTS 8,311,791 B1 11/2012 Avisar
11,571,266 B1 * 2/2023 Roh ...................... A61B 90/10
(Continued)

FOREIGN PATENT DOCUMENTS

CN 1871998 A 12/2006
CN 101332093 A 12/2008
(Continued)

OTHER PUBLICATIONS

Conti et al. ("Carotid artery hemodynamics before and after stenting: A patient specific CFD study," Computers and Fluids 141 (2016) 62-74 (Year: 2016).*
(Continued)

*Primary Examiner* — Soo Shin
(74) *Attorney, Agent, or Firm* — Lempia Summerfield Katz LLC (57) ABSTRACT

A system and method for deformation simulation of a hollow organ able to be deformed by the introduction of a medical instrument. The method includes provision of a pre-trained machine-learning algorithm, provision of a 3D medical recording of the hollow organ with surrounding tissue, with the 3D recording having been recorded before the introduction of a medical instrument, segmentation or provision of a segmentation of the 3D medical recording of the hollow organ and establishment or provision of a three-dimensional model of the hollow organ, provision of information about a medical instrument introduced or to be introduced, and simulation of the deformation of the hollow organ to be expected from introduction of the instrument on the basis of the segmented 3D medical recording of the hollow organ and of the surrounding tissue and of the information about the instrument by using the pre-trained machine-learning algorithm.

19 Claims, 5 Drawing Sheets

(51) Int. Cl.
  *G16H 30/40*   (2018.01)
  *G06F 30/27*   (2020.01)
  *G16H 70/60*   (2018.01)
  *G16H 50/50*   (2018.01)
  *G16H 50/70*   (2018.01)
  *G16H 50/20*   (2018.01)
  *G16H 40/63*   (2018.01)

(52) U.S. Cl.
  CPC ............ *G16H 40/63* (2018.01); *G16H 50/20* (2018.01); *G16H 50/50* (2018.01); *G16H 50/70* (2018.01); *G16H 70/60* (2018.01); *A61B 2034/104* (2016.02); *A61B 2034/107* (2016.02); *G06T 2207/20081* (2013.01)

(56) References Cited

U.S. PATENT DOCUMENTS

| | | | |
|---|---|---|---|
| 2003/0091967 | A1 | 5/2003 | Chosack et al. |
| 2004/0009459 | A1 | 1/2004 | Anderson et al. |
| 2008/0020362 | A1 | 1/2008 | Cotin et al. |
| 2008/0317195 | A1 | 12/2008 | Kobayashi et al. |
| 2009/0018808 | A1 | 1/2009 | Bronstein et al. |
| 2016/0310216 | A1* | 10/2016 | Van Bibber ............ A61B 34/10 |
| 2017/0357844 | A1 | 12/2017 | Comaniciu et al. |
| 2018/0000339 | A1* | 1/2018 | Hipsley ................. G16H 20/40 |
| 2018/0161099 | A1 | 6/2018 | Dumenil et al. |
| 2018/0308394 | A1* | 10/2018 | Segall ..................... G09B 23/28 |
| 2018/0308395 | A1 | 10/2018 | Kulkaski |
| 2019/0325572 | A1* | 10/2019 | Mansi .................. A61B 5/0077 |
| 2020/0188024 | A1* | 6/2020 | Breininger ............ A61B 90/92 |
| 2020/0311941 | A1* | 10/2020 | Sakuma ................. G16H 50/50 |
| 2021/0132687 | A1* | 5/2021 | Luo ......................... G06F 3/011 |

FOREIGN PATENT DOCUMENTS

| | | |
|---|---|---|
| CN | 103198202 A | 7/2013 |
| CN | 107067856 A | 8/2017 |
| CN | 107491633 A | 12/2017 |
| CN | 107705855 A | 2/2018 |
| CN | 109979600 A | 7/2019 |
| IN | 201737043218 A | 2/2018 |
| KR | 20160092799 A | 8/2016 |

OTHER PUBLICATIONS

Dr. Marcus Pfister, "Determining and taking account of calcifications in the visualization and deformation of segmentation meshes" 2019. pp. 1-2.

Koutouzi, Giasemi. Three-dimensional guidance for Endovascular Aortic Repair. 2017. pp. 1-87.

Pfister, Marcus, and Raul Rojas. "Hybrid learning algorithms for neural networks-the adaptive inclusion of second order information." (1996). pp.1-6.

Roy, David, et al. "Finite element analysis of abdominal aortic aneurysms: geometrical and structural reconstruction with application of an anisotropic material model." The IMA Journal of Applied Mathematics 79.5 (2014): 1011-1026.

Toth, Daniel, et al. "Adaption of 3D models to 2D x-ray images during endovascular abdominal aneurysm repair." International Conference on Medical Image Computing and Computer-Assisted Intervention. Springer, Cham, 2015. pp. 1-8.

Wikipedia: "Artificial neural network", Internet Article,, XP055385319, https://en.wikipedia.org/wiki/Artificial_neural_network; Aug. 2019. pp. 1-14.

\* cited by examiner

METHOD FOR DEFORMATION SIMULATION AND APPARATUS

CROSS REFERENCE TO RELATED APPLICATIONS

This application claims the benefit of EP 19189356.9 filed on Jul. 31, 2019, which is hereby incorporated by reference in its entirety.

FIELD

Embodiments relate to a method for deformation simulation of a hollow organ able to be deformed by the introduction of a medical instrument.

BACKGROUND

Figure 1:
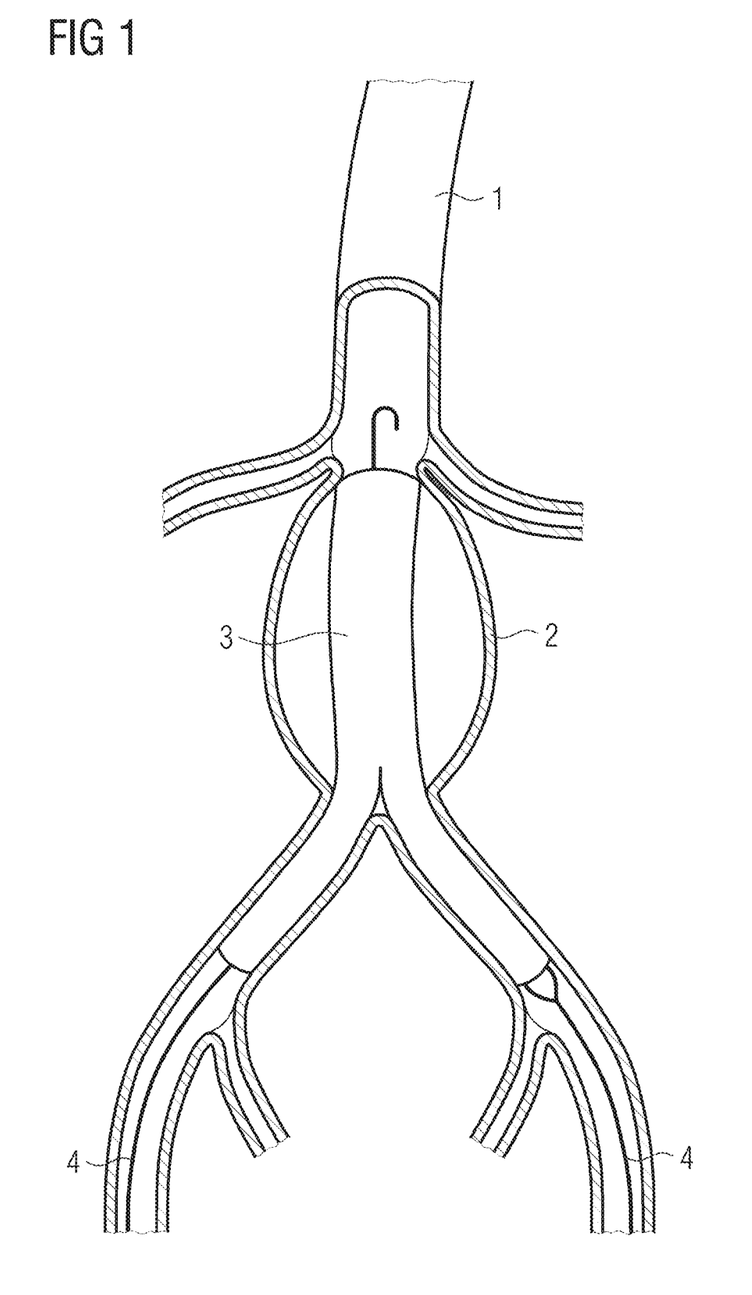
FIG. 1 depicts a view of an abdominal aortic aneurysm with inserted stent.

Deformation simulation may be used in the field of interventional treatment (e.g. repair) of aortic aneurysms. This may involve a non-linear adaptation of the vessels to inserted stiff instruments (such as guide wires, catheters, and stents), a deformation correction. An abdominal aortic aneurysm 2—see FIG. 1—is a bulging in the abdominal aorta 1, of which its extension into the leg arteries is referred to as an iliac aneurysm. This is treated either in an open abdomen operation or in a minimally invasive manner by insertion of what is known as a stent graft 3. Such a method is referred to as an EVAR=endovascular aneurysm repair. Guide wires 4 and catheters are inserted via the two branches into the abdominal aorta 1, via which one or more stent grafts 3 (combination of a stent and an artificial blood vessel) are inserted.

Figure 4:
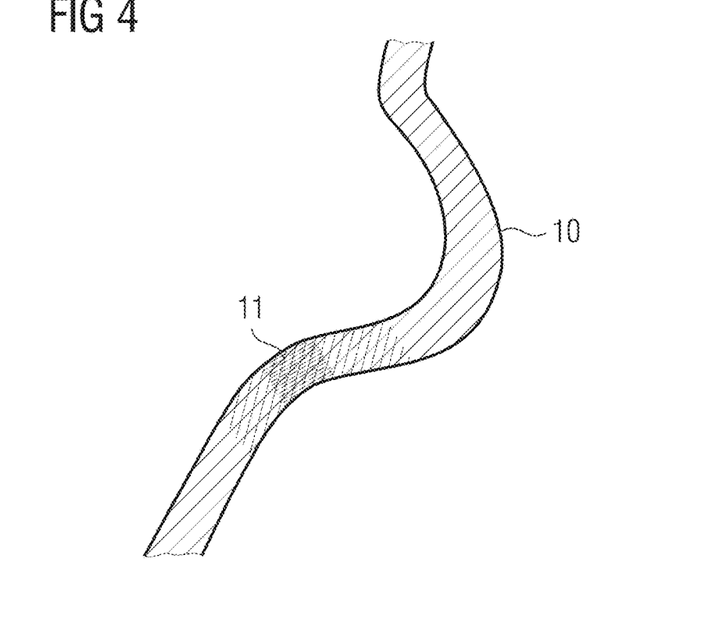
FIG. 4 depicts a view of a hollow organ cross-hatched according to stiffness.

EVAR procedures may be carried out on angiography systems under fluoroscopy control. Various methods are described for minimizing the application of contrast medium containing iodine (that damages the liver) in such procedures. The methods overlay datasets (for example, CT angiographs) registered with the fluoroscopy image. The CTA datasets are segmented beforehand for this purpose. In the sharply curved iliac vessels (also in the aorta) large deformations may occur through the introduction of the stiff instrument (such as guide wires and catheters for example). The deformations are principally a function of the local condition of the vessel and of the surrounding tissue, are thus not homogeneous. Thus, in calcified areas for example the vessel will deform less than in other areas. Shown in FIG. 4 is a hollow organ in which the heavily calcified region 11 includes dark cross-hatching.

Figure 2:
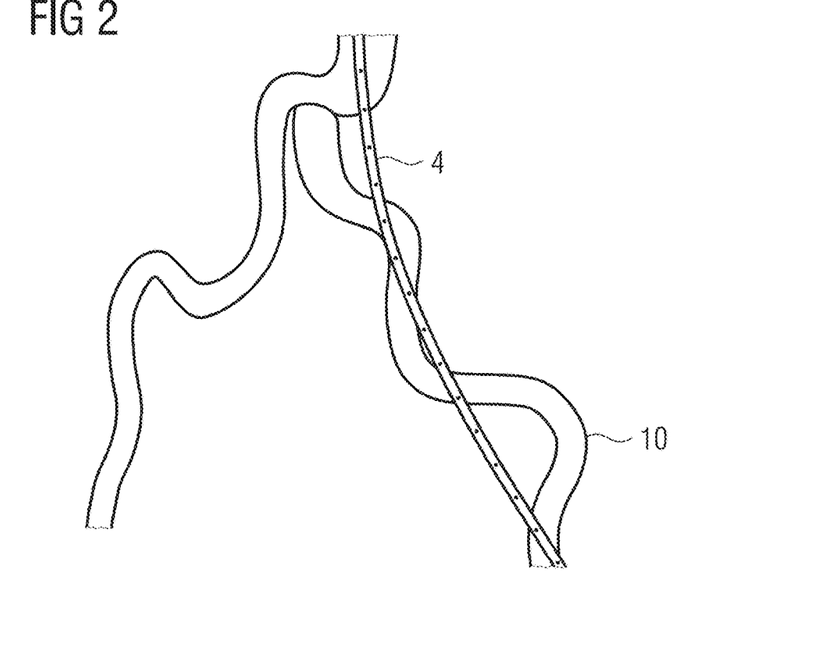
FIG. 2 depicts a view of an overlaying of a 3D recording of a hollow organ with a 2D image of a guide wire.
Figure 3:
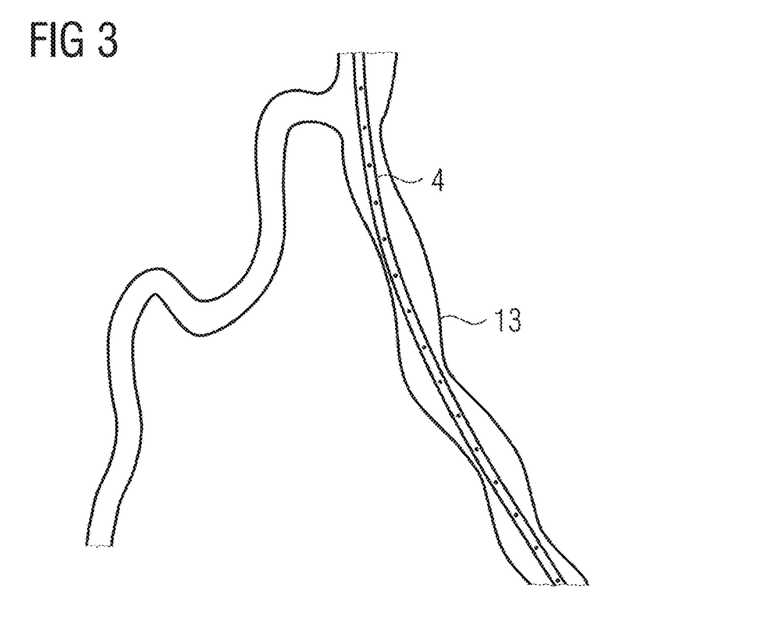
FIG. 3 depicts a view of a corrected position of the hollow organ.

Methods exist for compensating for this deformation intra-operatively in the overlaying. Thus, a method is known for example from the article by Toth et al., Adaptation of 3D Models to 2D X-ray Images during Endovascular Abdominal Aneurysm Repair, Proc. Of the MICCAI Workshop, 2015, pp. 339-346, for determining a deformation of a vessel using overlaid image datasets. An intraoperative deformation correction of this type is shown in FIGS. 2 and 3, wherein FIG. 2 depicts the original hollow organ 10 as well as the inserted guide wire 4 overlaid on one another. FIG. 3 depicts the corrected deformed hollow organ 13. Moreover methods exist that simulate the deformation pre-operatively, e.g. from the article by Roy et al., Finite element analysis of abdominal aortic aneurysms: geometrical and structural reconstruction with application of an anisotropic material model, IMA J Appl Math, 79 (5), 2014, pp. 1011-1026, where predetermined or measured properties of instruments and tissue are used for the simulation. This is however very complex and must be determined experimentally.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

Embodiments provide a simple and robust simulation of the deformation caused by the introduction of a medical instrument into a hollow organ.

In the method for deformation simulation of a hollow organ able to be deformed by the introduction of a medical instrument or medical object, the following steps are performed: Provision of a pre-trained machine-learning algorithm, Provision of a 3D medical recording of the hollow organ with surrounding tissue, with the 3D recording having been recorded before an introduction of a medical instrument or medical object, segmentation or provision of a segmentation of the 3D medical recording of the hollow organ and establishment or provision of a three-dimensional model of the hollow organ, provision of information about a medical instrument or medical object introduced or to be introduced, and simulation of the deformation of the hollow organ caused or to be expected from the introduction of the instrument or object on the basis of the segmented 3D medical recording of the hollow organ and of the surrounding tissue and of the information about the instrument or object through use of the pre-trained machine-learning algorithm.

The method provides a realistic and exact (3D) simulation of a deformation of a hollow organ by the introduction of a medical instrument or object to be created automatically quickly and with little effort, in that not the only hollow organ but also its surrounding tissue is included. The machine-learning algorithm for the simulation of the deformation of the hollow organ takes account of information about the influence of tissue properties of the surrounding tissue of the hollow organ. Calcifications around a hollow organ may have a highly decisive influence on the behavior of the hollow organ during the deformation for example, calcifications may make a deformation more difficult. The method uses this relationship and includes the tissue surrounding the hollow organ in the deformation simulation. In this way a pre-trained machine-learning algorithm includes an especially large amount of information available to it, that may have an influence on the deformation, so a qualitatively very high-value simulation may be achieved. This information for its part helps a doctor significantly in the therapy of a patient and in a decision about further treatment steps, e.g. in conjunction with interventional treatment of aortic aneurysms.

The method includes at least two applications: the method may serve, when an instrument/object is introduced, to simulate three-dimensionally the deformation of the hollow organ that is unknown because it is not visible in simple live fluoroscopy recordings, to obtain a precise image of the deformation. The method may also be used to simulate the deformation of the hollow organ before the instrument or object has been introduced, for example to be able to make a better decision about a planned intervention.

In an embodiment, the model of the hollow organ is formed by a surface or volume model. Models of this type have proved to be advantageous in the area of segmentation.

In an embodiment, the machine-learning algorithm is pre-trained by a plurality of known pairs of recordings from a first 3D medical recording of an undeformed hollow organ and of its surrounding tissue and a second 3D medical recording of a hollow organ deformed by a medical instrument and of its surrounding tissue. In its turn an effective pre-training of the algorithm is possible by way of as many high-quality (3D) pairs of recordings as possible, whereby in its turn an exact simulation may then be brought about.

In an embodiment, the pairs of recordings are each segmented in relation to the hollow organ and the hollow organ is represented as a three-dimensional model with sub-elements, for example as a grid with grid elements. An automatic or semi-automatic pre-segmentation of the hollow organ is a method that considerably facilitates the further processing of 2D or 3D recordings, in that specific structures (i.e. the hollow organ for example) are recognized and marked or highlighted for example. Subsequently the hollow organ segmented in this way may be represented as a model including a plurality of sub-elements. A grid with grid elements is used. The sub-elements may be configured as polygons, splines, or other suitable mathematical formulations.

In an embodiment, the machine-learning algorithm takes stiffness parameters between sub-elements into account for the simulation of the deformation of the hollow organ. The stiffness parameters are taken from the 3D medical recording as parameterized functions of the tissue properties of the surrounding tissue of the respective sub-elements. Stiffness parameters refer to parameters that represent a measure for the deformability of materials. The appropriate stiffness parameters are established within the framework of pre-training.

In an embodiment, the stiffness parameters bring about a minimization of the error between real deformation (also of a hollow organ from an actually recorded 3D recording deformed by the medical instrument and its surrounding tissue) and deformation simulation within the framework of the pre-training. The error minimization that is established by pairs of recordings from a first 3D medical recording of an undeformed hollow organ and its surrounding tissue and a second 3D medical recording of a hollow organ deformed by a medical instrument and its surrounding tissue, provides the stiffness parameters to be determined that bring about an especially realistic deformation simulation.

In an embodiment, the characteristics of the tissue surrounding the model are mapped on the model. The characteristics may influence the local deformation behavior of the hollow organ. In this context different alternatives may be chosen, that depending on the model, the hollow organ, and the surrounding tissue, may provide a high-quality deformation simulation. Thus, with an especially easy-to-implement variant, the surrounding tissue of a sub-element may be mapped by a vector of prespecified length on the sub-element. With a second exact variant, the surrounding tissue of a sub-element may be mapped by a hemispherical circumcircle with a prespecified radius on the sub-element.

In an embodiment, tissue characteristics are represented by Hounsfield units, for example, for the case in which the 3D medical recording is a CT or DynaCT recording. The Hounsfield scale describes the attenuation of x-ray radiation in tissue, the values may then be assigned to tissue types/characteristics for example.

In an embodiment, the algorithm is trained on the basis of pairs of recordings, in which the second 3D medical recording is replaced by a second, physically motivated simulation of a deformation, e.g. by FE methods. In this way the algorithm may be trained to reproduce such a simulation exactly.

In an embodiment, the deformation simulation is displayed on a display apparatus, so that for example the deformation simulation may be appraised by a doctor. The doctor may then, on the basis of the displayed deformation simulation, decide on the actual intervention and make a change if necessary.

In an embodiment, the deformation simulation is overlaid with at least one 2D recording, for example a live fluoroscopy recording. This is advantageous if a planned or actual interventional procedure will take place with x-ray monitoring. The introduced medical instrument/object may be mapped on the two-dimensional live fluoroscopy recording for example.

In an embodiment, the information about the medical instrument introduced or to be introduced may be taken from a 2D recording, for example a fluoroscopy recording. The 2D recording may be obtained from a memory or recorded live. The 2D recording may be subjected to image processing and be segmented in respect of the instrument. On the basis of a live fluoroscopy recording the current position, the actual course and also the current deflection of the instrument may be obtained. From a recording previously made and stored for example information about the form and length of the instrument may be obtained. The information is then made available to the deformation simulation. This process may also be carried out automatically. The information made available is then used in the method.

The medical instrument or object to be introduced may involve a guide wire or a vascular support.

The machine learning, for example deep learning-based algorithm may be formed for example from one or more neural networks and operate for example by semi-supervised learning methods or reinforcement learning.

If the instrument or object is not yet introduced, then as well as information about the form, size, position etc., information about characteristics of the instrument or object is also used, e.g. the stiffness, hardness etc. This may be taken from a memory for example or entered. Moreover, information about the desired position is used, that may be defined or entered beforehand for example.

Embodiments provide a system for carrying out a deformation simulation of a hollow organ of a patient able to be deformed by the introduction of a medical instrument or medical object. The system includes a communication apparatus for interrogating 3D medical recordings of the hollow organ with surrounding tissue, a storage apparatus for storage of 3D medical recordings of the hollow organ with surrounding tissue, an image processing apparatus for carrying out a segmentation of 3D medical recordings of the hollow organ with surrounding tissue and for establishment of a three-dimensional model of the surface of the hollow organ with surrounding tissue, a pre-trained machine-learning algorithm that is configured to simulate the deformation of the hollow organ brought about or to be expected by the introduction of the instrument or object on the basis of a segmented 3D medical recording, a processing facility with a processor configured to carry out the pre-trained machine-learning algorithm, and a display apparatus configured to display the modeled hollow organ deformed by the instrument or object. The system may include an angiography x-ray device for recording a 3D medical recording of hollow organs with surrounding tissue.

DETAILED DESCRIPTION

Figure 5:
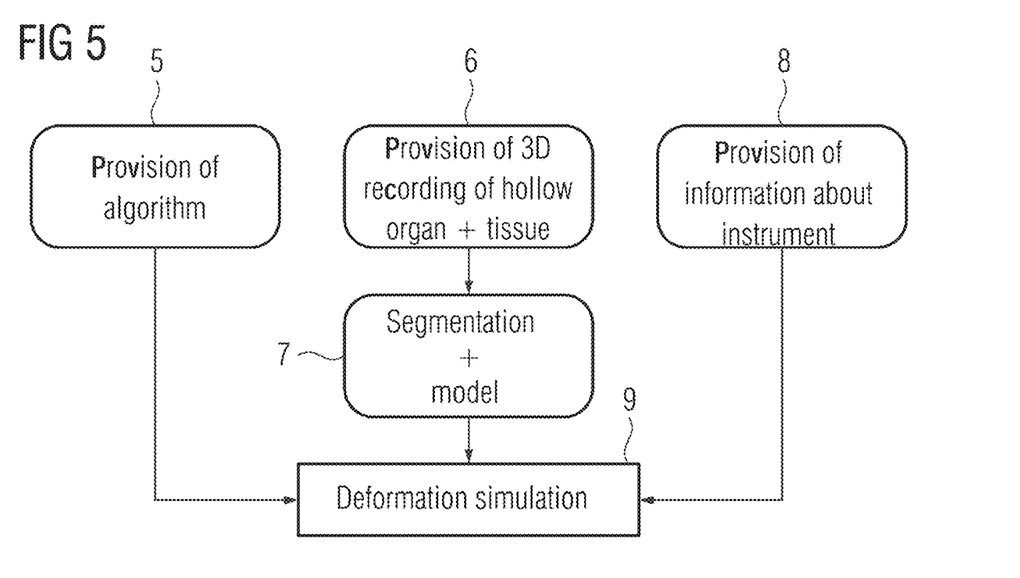
FIG. 5 depicts an execution sequence of a method according to an embodiment.

Shown in FIG. 5 are steps of the method for deformation simulation of a hollow organ that may be deformed by the introduction of a medical instrument. The method is carried out for example before the start of an interventional procedure on the hollow organ. The intervention may be carried out for example within the framework of an interventional treatment (e.g. repair) of an aortic aneurysm. The method may also take place in the operating theater when the interventional procedure has already been carried out and the instrument or object is introduced, to be able to map three-dimensionally the deformation of the hollow organ, unknown because it is not visible in simple live fluoroscopy recordings.

In a first step 5 a pre-trained machine-learning algorithm, e.g. deep learning algorithm, is provided. Different possibilities and influences of the pre-training of the machine-learning algorithm will be described later in detail. The machine-learning algorithm may be formed by an artificial neural network for example. Neural networks that are constructed as networks of artificial neurons are generally known.

In a second step 6 at least one 3D medical recording of the hollow organ with its surrounding tissue, with the 3D recording being recorded before an introduction of a medical instrument, is provided. The 3D recording may have been created by an x-ray device, e.g. an angiography x-ray device or a computed tomography unit. As an alternative the 3D recording may also be produced directly.

In a third step 7 the 3D medical recording of the hollow organ is segmented directly or is provided in already segmented form. In this case a three-dimensional model of the hollow organ is established or is already provided in the form of a model. A surface model or also a volume model may be used as the model for the hollow organ. For example, a polygon mesh with mesh elements in the form of polygons or a surface model based on splines may be used as the surface model.

In a fourth step 8 information about the medical instrument introduced or to be introduced is provided. The instrument or object may involve a catheter or a guide wire or a vascular support to be introduced for example. The information may be taken from a database/a memory, entered by a user, or be taken from a directly (or previously) recorded 2D recording (live fluoroscopy recording) or 3D recording for example. The first step 5, the second step 6 and the fourth step 8 in this case may be in any given order.

The 2D recording may be subjected to image processing and segmented in respect of the instrument. On the basis of the live fluoroscopy recording the current position, the actual course, and the actual deflection of the introduced instrument may be obtained. Information about the form and length of the instrument may be obtained from a previously recorded and stored recording for example.

If the instrument or object is not yet introduced and the deformation of the hollow organ is basically to be simulated with the instrument/object not yet introduced by the method, then as an alternative or in addition information on the intended position of the instrument or object is used. Instead of or in addition to information about three-dimensional layout (form, size, thickness etc.) of the instrument or object, characteristics, e.g. stiffness or hardness, may also be used.

The information about the instrument or object is made available to the deformation simulation. The process may also be carried out automatically.

In a subsequent fifth step 9, with the aid of the pre-trained machine-learning algorithm using the segmented 3D medical recording of the hollow organ and using information about the surrounding tissue and using the information about the instrument, the deformation of the hollow organ caused or to be expected by the introduction of the instrument is simulated. The influence of the surrounding tissue on the respective deformation model is determined by a machine-learning or self-learning algorithm to obtain a high-quality three-dimensional deformation simulation of the hollow organ or to improve a deformation correction.

In the case of an instrument or object not yet being introduced, its deformation may moreover additionally be simulated at the same time.

The deformation simulation(s) may be displayed on a display unit 22.

Figure 6:
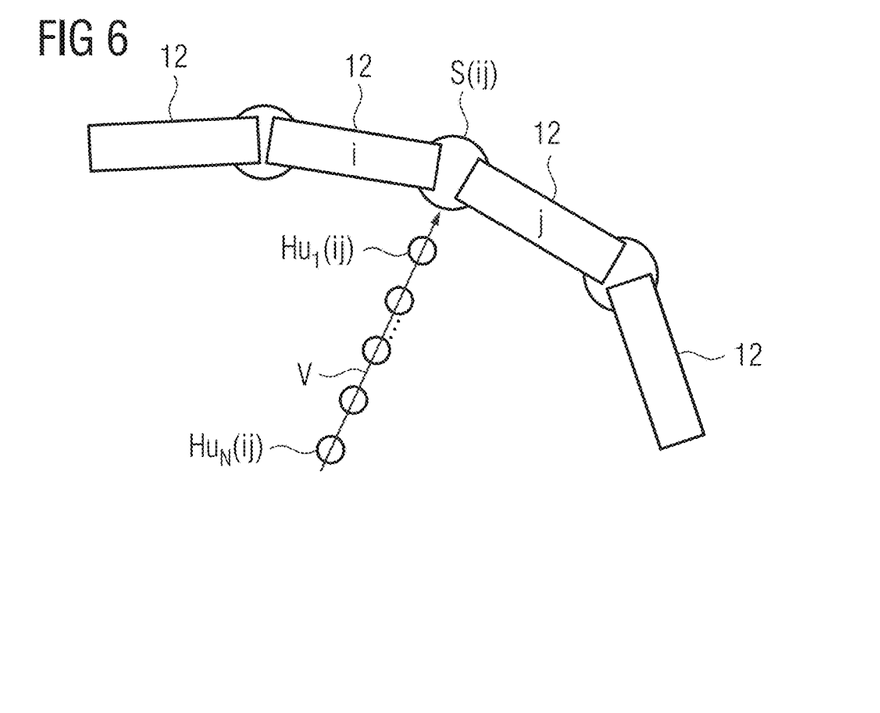
FIG. 6 depicts a diagram of a stiffness parameter and Hounsfield units projected thereon according to an embodiment.
Figure 7:
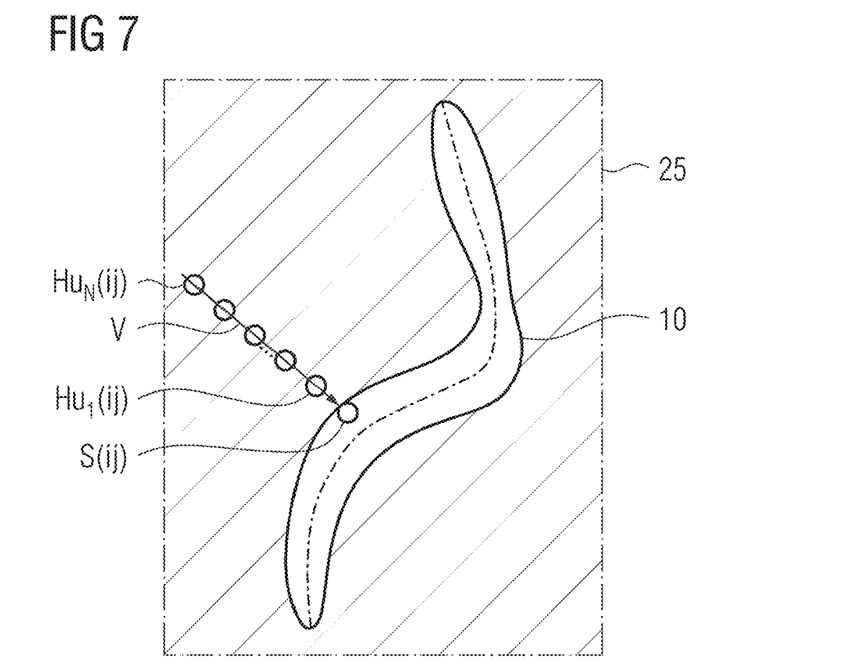
FIG. 7 depicts a 2D view of an undeformed recording with segmented hollow organ and surrounding tissue for obtaining Hounsfield units according to an embodiment.

Described below are underlying mathematical ideas and details of the deformation simulation. The three-dimensional model of the hollow organ with sub-elements below is a polygon mesh with polygons as mesh elements. However, any other models with sub-elements may be used. The stiffness parameter S(ij) of the model of the hollow organ between the ith polygon i and the jth polygon j designate the measure for the deformability of the hollow organ—shown in FIG. 6. If a transformation specification T of the deformation simulation is described, this produces $$MM=T[S,MO]$$

where MO refers to the original undeformed segmentation, MM to the corresponding simulation and S to the totality of the stiffness parameters S(ij).

The influence of the surrounding tissue on the deformation (thus in the deformation simulation the stiffness of the polygons relative to one another) is learned on the basis of a set of available data, known as training data. A set M of known pairs of recordings of a first 3D medical recording of an undeformed hollow organ and its surrounding tissue MO_gt and a second 3D medical recording of a hollow organ and its surrounding tissue MM_gt deformed by a medical instrument serves as training data. To this end the stiffness parameters S(ij) are formulated as a parameterized function of the surrounding tissue Gew(ij):

$$S(ij)=F(W,Gew(in)$$

The optimum weights $W_{opt}$ are "learned" on the basis of the set M of known pairs of recordings $$TM=\{(MO\_gt(k),MM\_gt(k)),k=1,\ldots,M\}$$

Here the optimum weights $W_{opt}$ are determined that cause a minimization of the error between real deformation and simulated deformation for the set M. If the optimum weights are determined, the deformation simulation for any given 3D recording of an undeformed hollow organ and its surrounding tissue MO is able to be calculated as $$MM=T[F(W_{opt},Gew),MO].$$

For further implementation of the method, for concrete evaluation of the function, the tissue environment Gew(ij) may be expressed for example as discrete sampling Gew(ij)=[$G_{1(ij)}, G_{2(ij)}, \ldots G_{N(ij)}$] of a certain environment between the ith polygon i and the jth polygon j, i.e.

$$S(ij)=F(W,[G_{1(ij)},G_{2(ij)}, \ldots ,G_{k(ij)}),G_{N(ij)}]).$$

Since the polygons needed for the deformation simulation (sub-elements or grid elements) are embedded in the 3D recording of the hollow organ and its surrounding tissue, it is further assumed for concrete calculation that different tissue (characteristics) are represented by different Hounsfield units (HU), i.e. that $G_{k(ij)}=HU_{k(ij)}$ applies. It is of no significance here that the same tissue may create a spectrum of Hounsfield units (HUs) or that different tissue may be mapped by the same HU value.

For the modeling of the stiffness parameters S(ij) the (still unknown) function is produced $$S(ij)=F(W,[HU_{1(ij)},HU_{2(ij)}, \ldots ,HU_{k(ij)}, \ldots HU_{N(ij)}]).$$

FIG. 6 depicts schematically how the surrounding tissue is mapped by a vector V of predetermined length on the polygon (grid element, sub-element) with the stiffness S(ij), wherein die tissue characteristics at different points 1 . . . N are represented by Hounsfield units $HU_{1(ij)} \ldots HU_{N(ij)}$. As an alternative to the vector V the surrounding tissue of a sub-element may for example also be mapped by a hemispherical circumcircle with a predetermined radius on the sub-element.

For a given transformation specification T for deformation simulation (e.g. ARAP or an FEM modeling) the following is thus produced for the transformation overall:

$$MM=T[S,MO]=T[F(W,HU),MO]$$

The parameters $W_{opt}$ are learned on the basis of the minimization of the corresponding error function on a set of M known pairs of recordings form a first 3D medical recording of an undeformed hollow organ and its surrounding tissue MO_gt and a second 3D medical recording of a hollow organ and its surrounding tissue MM_gt deformed by a medical instrument $$W_{opt}=\mathrm{argmin}_W \Sigma_{k=1}^M \|(MM_{gt(k)}-T[[W/HU],MO_{gt}t(k)])\|$$

Corresponding learning processes are used for determination, e.g. backpropagation with gradient descent method or other methods for non-linear optimization. Such methods are known for example from the article by Pfister et al. *Hybrid learning algorithms for neural networks*, Zeitschrift für Angewandte Mathematik und Mechanik (Journal of Applied Mathematics and Mechanics), Vol. 76, Suppl. 1, 1996, pp. 215ff.

For training the machine-learning algorithm a sufficiently large set of M known pairs of recordings TM={(MO_gt(k), MM_gt(k)), k=1, . . . , M} is needed. Such pairs of recordings may be obtained for example from deformed intraoperative 3D recordings (DynaCT, angio recordings etc.) and their undeformed counterparts. As an alternative the real 3D recording may also be replaced by a physically motivated simulation, e.g. by FE methods.

For training of the algorithm, the characteristics (e.g. stiffness, hardness etc.) of the instrument or object may also be entered and taken into account.

It may occur that the deformation is not known completely and accurately for all polygons from the second 3D medical recording of a hollow organ and its surrounding tissue deformed by a medical instrument. In such case the weights may also be learned based on subsets and/or approximately known deformations. Here for example semi-supervised learning methods or reinforcement learning may be used.

The method may be employed in all possible areas of application for the adaptation of segmentation deformations of hollow organs, e.g. in neuroradiology, the insertion of aortic valves or the deformation of vessels in the liver. Both x-ray recordings and also 3D recordings recorded by other medical imaging methods, e.g. MR recordings, and segmented accordingly may be used as 3D recordings of the hollow organ with surrounding tissue. The values are not able to be interpreted as HU values, but may otherwise be used in a similar way.

The information about the medical instrument introduced or to be introduced may be taken from a 2D recording, for example a fluoroscopy recording. The 2D recording may be obtained from a memory of recorded live for example. The 2D recording may be subjected to image processing and segmented in respect of the instrument. The information is then made available to the deformation simulation. This process may also be carried out automatically. The medical instrument or object to be introduced may, for example, involve a guide wire or a vascular support.

The information about the medical instrument introduced or to be introduced may be taken from a memory or entered. Instead of or in addition to information about three-dimensional layout (form, size, thickness etc.) of the instrument or object, characteristics, e.g. stiffness or hardness may also be used. This applies both for the training of the algorithm and also for the method itself. The information may thus be learned during the training of the algorithm and/or be taken into account when carrying out the method.

Figure 8:
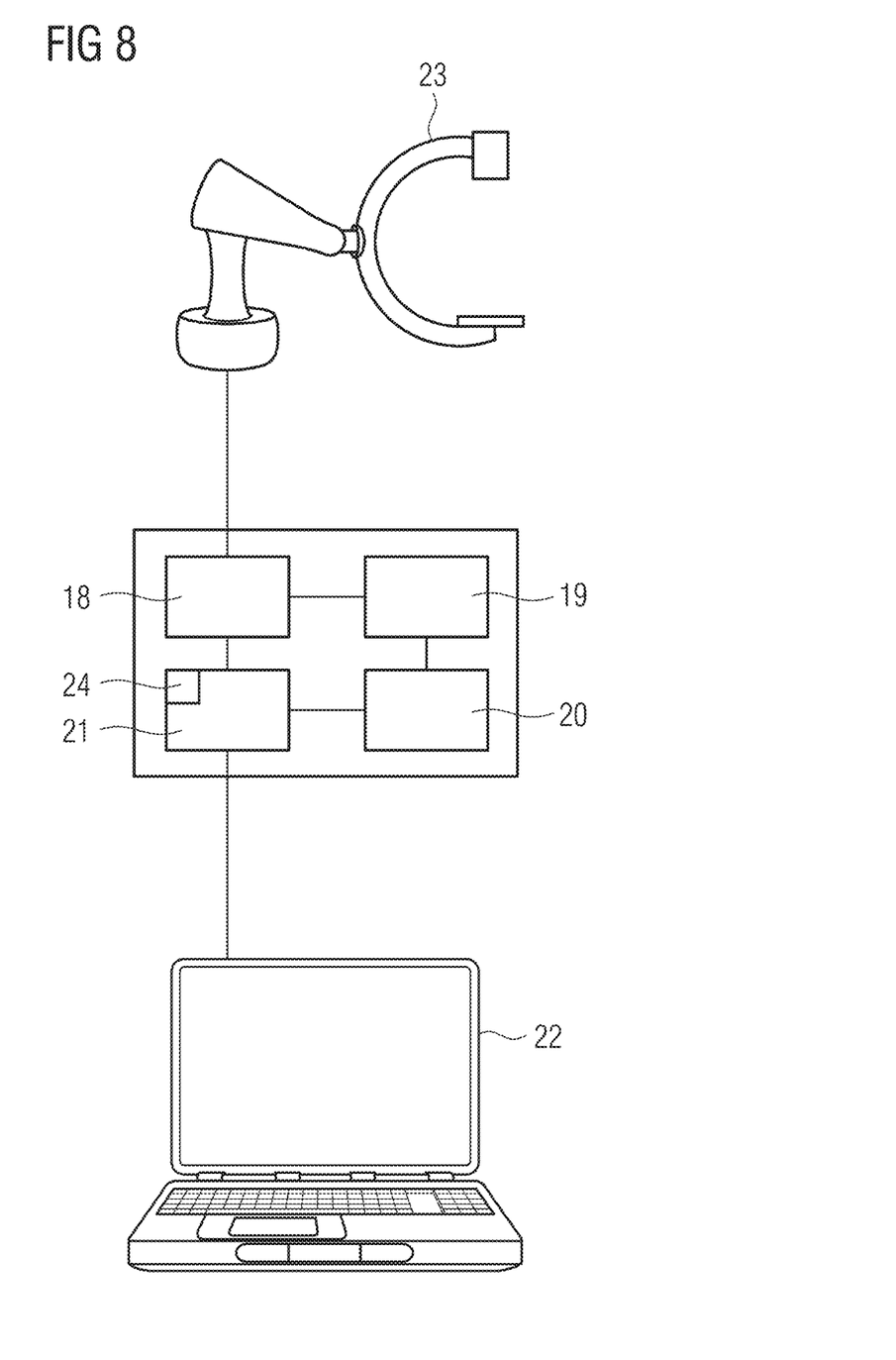
FIG. 8 depicts a system for carrying out the method according to an embodiment.

Shown in FIG. 8 is a system for carrying out a deformation simulation of a hollow organ of a patient that may be deformed by the introduction of a medical instrument. The system includes a processing facility 21 with a processor. The processing facility 21 is configured to execute a pre-trained machine-learning algorithm 24 that is configured to simulate on the basis of a segmented 3D medical recording the deformation of the hollow organ to be expected from the introduction of the instrument. The system includes a communication apparatus 18 for interrogation of 3D medical recordings of the hollow organ with surrounding tissue, a storage apparatus 19 for storage of 3D medical recordings of the hollow organ with surrounding tissue and an image processing apparatus 20 for carrying out a segmentation of 3D medical recordings of the hollow organ with surrounding tissue and for establishment of a three-dimensional model of the surface of the hollow organ with surrounding tissue. A display apparatus 22 for display of the modeled hollow organ deformed by the instrument is assigned to the system. The system may be assigned to an angiography x-ray device 23 for recording a 3D medical recording of hollow organs with surrounding tissue.

The method for deformation simulation using a machine-learning algorithm includes not having to experimentally determine in an error-prone and complex manner the influence of tissue on the deformation simulation, as was usually the case previously, but being able to train it in a simple and robust manner on the basis of examples.

For an especially simple and simultaneous exact deformation simulation of a hollow organ able to be deformed by the introduction of a medical instrument or medical object the following steps are carried out: Provision of a pre-trained machine-learning algorithm, provision of a 3D medical recording of the hollow organ with surrounding tissue, with the 3D recording having been recorded before an introduction of a medical instrument or medical object, segmentation or provision of a segmentation of the 3D medical recording of the hollow organ and establishment or provision of a three-dimensional model of the hollow organ, provision of information about a medical instrument or medical object introduced, and simulation of the deformation of the hollow organ caused or to be expected from the introduction of the instrument on the basis of the segmented 3D medical recording of the hollow organ and of the surrounding tissue and the information about the instrument or object by using the pre-trained machine-learning algorithm.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for deformation simulation of a hollow organ that is deformed by an introduction of a medical instrument or a medical object, the method comprising:
   providing a pre-trained machine-learning algorithm, wherein the machine-learning algorithm is pre-trained by a plurality of known pairs of recordings from a first three-dimensional medical recording of an undeformed hollow organ and its surrounding tissue and a second three-dimensional medical recording of a hollow organ and its surrounding tissue deformed by a medical instrument or a medical object;
   acquiring a three-dimensional medical recording of the hollow organ with surrounding tissue, wherein the three-dimensional medical recording was recorded before the introduction of the medical instrument or the medical object;
   segmenting or acquiring a segmentation of the three-dimensional medical recording of the hollow organ;
   forming or acquiring a three-dimensional model of the hollow organ;
   providing information about the medical instrument or the medical object introduced or to be introduced; and
   simulating, using the pre-trained machine-learning algorithm, a deformation of the hollow organ to be expected or brought about by introduction of the medical instrument or the medical object on a basis of the segmented three-dimensional medical recording of the hollow organ and the surrounding tissue and the information about the medical instrument or the medical object.

2. The method of claim 1, wherein the three-dimensional model is formed by a surface model or volume model.

3. The method of claim 1, wherein the machine-learning algorithm takes account of information about an influence of tissue characteristics of the surrounding tissue of the hollow organ for the simulation of the deformation of the hollow organ.

4. The method of claim 1, wherein the pairs of recordings are each segmented in relation to the hollow organ and the hollow organ is represented as the three-dimensional model with a plurality of sub-elements.

5. The method of claim 4, wherein the three-dimensional model is a mesh model with mesh elements.

6. The method of claim 4, wherein the surrounding tissue of a sub-element of the plurality of sub-elements is mapped by a vector of predetermined length on the sub-element.

7. The method of claim 4, wherein the surrounding tissue of a sub-element of the plurality of sub-elements is mapped by a hemispherical circumcircle with a predetermined radius on the sub-element.

8. The method of claim 4, wherein the plurality of sub-elements are mapped as polygons, splines, or other mathematical formulations.

9. The method of claim 1, wherein the machine-learning algorithm takes account of stiffness parameters between a plurality of sub-elements for the deformation simulation of the hollow organ, with the stiffness parameters being taken from the three-dimensional medical recording as parameterized functions of tissue characteristics of the surrounding tissue.

10. The method of claim 9, wherein the stiffness parameters are established that bring about a minimization of an error between real deformation and deformation simulation.

11. The method of claim 1, wherein characteristics of the tissue surrounding the three-dimensional model are mapped on the three-dimensional model, wherein the characteristics influence a local deformation behavior of the hollow organ.

12. The method of claim 1, wherein tissue characteristics are represented by Hounsfield units.

13. The method of claim 1, wherein the machine-learning algorithm is trained on the basis of the pairs of recordings in that an error function as the error between actual and simulated deformation is minimized.

14. The method of claim 1, wherein the machine-learning algorithm is trained on the basis of the pairs of recordings in that the second three-dimensional medical recording is replaced by a second simulation provided by finite element (FE) methods.

15. The method of claim 1, further comprising:
   displaying the deformation simulation on a display apparatus.

16. The method of claim 15, wherein the deformation simulation is overlaid with at least one two-dimensional recording.

17. The method of claim 16, wherein the deformation simulation is overlaid with a live fluoroscopy recording.

18. The method of claim 1, further comprising
   simulating a deformation of the medical instrument or the medical object.

19. A system for performing a deformation simulation of a hollow organ of a patient able that is deformed by an introduction of a medical instrument or medical object, the system comprising:
   a communication apparatus configured to interrogate three-dimensional medical recordings of the hollow organ with surrounding tissue;
   a storage apparatus configured to store three-dimensional medical recordings of the hollow organ with surrounding tissue;

an image processor configured to segment three-dimensional medical recordings of the hollow organ with surrounding tissue and to establish a three-dimensional model of a surface of the hollow organ with surrounding tissue;
a processor configured to simulate, using a pre-trained machine-learning algorithm, the deformation of the hollow organ to be expected or caused by the introduction of the medical instrument on a basis of a segmented three-dimensional medical recording, wherein the machine-learning algorithm is pre-trained by a plurality of known pairs of recordings from a first three-dimensional medical recording of an undeformed hollow organ and its surrounding tissue and a second three-dimensional medical recording of a hollow organ and its surrounding tissue deformed by a medical instrument or a medical object; and
a display configured to display the simulated hollow organ deformed by the medical instrument or the medical object.

* * * * *

UNITED STATES PATENT AND TRADEMARK OFFICE
CERTIFICATE OF CORRECTION

Page 1 of 1

PATENT NO. : 11,883,108 B2
APPLICATION NO. : 16/943037
DATED : January 30, 2024
INVENTOR(S) : Katharina Breininger and Marcus Pfister It is certified that error appears in the above-identified patent and that said Letters Patent is hereby corrected as shown below:

In the Claims (Claim 19; Line 59):
"a hollow organ of a patient able that is deformed by an"
Should be replaced with:
"a hollow organ of a patient that is deformed by an"

Signed and Sealed this
Second Day of April, 2024

Katherine Kelly Vidal
*Director of the United States Patent and Trademark Office*